United States Patent [19]
Van Phan

[11] Patent Number: 5,487,736
[45] Date of Patent: Jan. 30, 1996

[54] MULTI-TOPOGRAPHY SUBSTRATE HAVING SELECTIVELY DISPOSED OSMOTIC ABSORBENT, INCORPORATION THEREOF IN A DISPOSABLE ABSORBENT ARTICLE AND PROCESS OF MANUFACTURE THEREFOR

[75] Inventor: Dean Van Phan, West Chester, Ohio

[73] Assignee: The Procter & Gamble Company, Cincinnati, Ohio

[21] Appl. No.: 435,556

[22] Filed: May 5, 1995

Related U.S. Application Data

[63] Continuation of Ser. No. 153,863, Nov. 17, 1993, abandoned.

[51] Int. Cl.⁶ .............................. A61F 13/15; A61F 13/20
[52] U.S. Cl. ......................... 604/368; 604/372; 604/384
[58] Field of Search .................................. 604/358, 367, 604/368, 365, 372, 378–381, 384, 385.1

[56] References Cited

U.S. PATENT DOCUMENTS

| | | | |
|---|---|---|---|
| 3,554,788 | 1/1971 | Fechillas | 604/372 |
| 3,965,904 | 6/1976 | Mesek et al. | 604/380 |
| 3,993,820 | 11/1976 | Repke | 604/380 |
| 4,008,353 | 2/1977 | Gross et al. | |
| 4,061,846 | 12/1977 | Gross et al. | |
| 4,071,650 | 1/1978 | Gross | |
| 4,082,878 | 4/1978 | Boe et al. | |
| 4,145,464 | 3/1979 | McConnell et al. | |
| 4,293,600 | 10/1981 | Fink et al. | |
| 4,310,593 | 1/1982 | Gross | 428/290 |
| 4,354,487 | 10/1982 | Oczkowski et al. | |
| 4,715,918 | 12/1987 | Lang | |
| 4,748,076 | 5/1988 | Saotome | |
| 4,820,294 | 4/1989 | Morris | 604/383 |
| 4,835,020 | 5/1989 | Itoh et al. | |
| 4,842,927 | 6/1989 | Itoh et al. | |
| 4,865,886 | 9/1989 | Itoh et al. | |
| 4,888,238 | 12/1989 | Katz et al. | |
| 4,892,754 | 1/1990 | Itoh et al. | |
| 4,994,053 | 2/1991 | Lang | 604/367 |
| 5,013,309 | 5/1991 | Baigas, Jr. et al. | |
| 5,071,681 | 12/1991 | Manning et al. | |
| 5,079,034 | 1/1992 | Miyake et al. | |
| 5,175,046 | 12/1992 | Nguyen | |

FOREIGN PATENT DOCUMENTS

| | | | |
|---|---|---|---|
| 0040087A2 | 11/1981 | European Pat. Off. | |
| 0160572 | 11/1985 | European Pat. Off. | 604/358 |
| 0262405 | 8/1987 | European Pat. Off. | |
| 0257308 | 3/1988 | European Pat. Off. | |
| 0291316A2 | 11/1988 | European Pat. Off. | |
| 0290814 | 11/1988 | European Pat. Off. | |
| 0293762 | 12/1988 | European Pat. Off. | |
| 0304952 | 3/1989 | European Pat. Off. | |
| 2222780 | 11/1973 | Germany | |
| 63-291908 | 11/1988 | Japan | |
| 1452325 | 10/1976 | United Kingdom | |

Primary Examiner—Randall L. Green
Assistant Examiner—P. Zuttarelli
Attorney, Agent, or Firm—Larry L. Huston; E. Kelly Linman; Jacobus C. Rasser

[57] ABSTRACT

An absorbent structure having both osmotic and capillary absorbing capabilities. The substrate has a topography comprising two different elevations. The osmotic absorbent structure may include superabsorbents and is preferentially applied to the high elevation regions of the substrate. This arrangement provides for better acquisition of liquids without gel blocking. The absorbent structure is suitable for use in the cores of disposable absorbent articles.

19 Claims, 2 Drawing Sheets

MULTI-TOPOGRAPHY SUBSTRATE HAVING SELECTIVELY DISPOSED OSMOTIC ABSORBENT, INCORPORATION THEREOF IN A DISPOSABLE ABSORBENT ARTICLE AND PROCESS OF MANUFACTURE THEREFOR

This is a continuation of application Ser. No. 08/153,863, filed on Nov. 17, 1993 now abandoned.

FIELD OF THE INVENTION

This invention relates to a substrate have plural topographies of different elevations. More particularly, an osmotic absorbent is selectively disposed on regions of the substrate corresponding to a particular topography. The substrate may be a capillary absorbent substrate.

BACKGROUND OF THE INVENTION

Absorbent structures comprising a substrate, and frequently a capillary absorbent substrate are known in the art. As used herein, a "capillary" absorbent structure absorbs liquids, such as water, by capillary attraction of the liquids due to the thermodynamic force of attraction between a liquid and the solid surface of the capillary medium.

Frequently an osmotic absorbent is applied to or otherwise disposed on the substrate. As used herein, an "osmotic" absorbent structure absorbs liquids deposited thereon by equalization of differential partial fluid pressure in the absence of ion exchange, forming a gelatinous substance which imbibes the liquids. As used herein, an "absorbent structure" refers to materials which, in combination, absorb liquids by both osmotic and capillary absorptions.

The osmotic absorbent may be made from monomers selected from the group consisting of acrylic acid, starch grafted acrylate co-polymers, etc. Such osmotic absorbent materials are commonly used as absorbent gelling materials or superabsorbers in disposable absorbent articles such as diapers and sanitary napkins. The osmotic absorbent may be applied to the substrate in the form of a liquid precursor, to be later cured into an osmotic absorbent.

The capillary absorbent may be provided in the form of a substrate, for the osmotic absorbent to be later applied thereupon. Typically the capillary absorbent substrate is a generally planar, almost two-dimensional material, such as paper, nonwoven fabric, woven fabric, or even formed film.

Generally, the osmotic absorbent material may be applied to the capillary absorbent substrate as a fluid precursor, such as a liquid monomer, then crosslinked to form an absorbent polymeric material. Usually, the liquid precursor is applied to the capillary absorbent substrate in a fluid form and typically comprises some form of acrylic acid and acrylate salts.

Typically, the liquid precursor is applied to the absorbent substrate by spraying, impregnation, etc. to provide a uniform coating thereon. Other teachings in the art suggest discontinuous applications of the liquid precursor to the substrate through brushing, roller coating, etc. Once the liquid precursor is applied to the capillary absorbent substrate, the liquid precursor may be crosslinked through elevated temperature, irradiation, etc.

Examples of such attempts in the art include U.S. Pat. Nos. 4,008,353 issued Feb. 15, 1977 to Gross et al.; 4,061,846 issued Dec. 6, 1977 to Gross et al.; 4,071,650 issued Jan. 31, 1978 to Gross; 4,835,020 issued May 30, 1989 to Itoh et al.; 4,842,927 issued Jun. 27, 1989 to Itoh et al.; 4,865,886 issued Sep. 12, 1989 to Itoh et al; 4,892,754 issued Jan. 9, 1990 to Itoh et al.; 5,079,034 issued Nov. 21, 1988 to Miyake et al. and Great Britain Patent 1,452,325 published October, 1976 in the name of Triopolis.

However, these attempts in the art suffer from serious drawbacks. As is all too well known in the art, when an osmotic absorbent imbibes liquids, the osmotic absorbent swells in volume. If such swelling occurs too rapidly, the increase in volume of the osmotic absorbent which has imbibed liquids may prevent later liquid insults from reaching portions of the osmotic absorbent which are still able to absorb liquids. This phenomenon, known as gel blocking, may prevent further absorption of liquids. Gel blocking often prevents the absorbent structure from utilizing its total capacity. If an absorbent structure which encounters gel blocking is used in a disposable absorbent article, such as a diaper or sanitary napkin, and liquid insults occur after the gel blocking, such insults may not be absorbed and leakage may result.

Clearly from this standpoint, a uniform coating of the liquid precursor material on the capillary substrate can be very undesirable. However, a high surface area to mass ratio of the osmotic absorbent generally increases the rate of absorbency. Therefore, to minimize gel blocking a thin nonuniform coating of the osmotic absorbent may be applied to the capillary substrate as is known in the art.

Typically, the capillary substrate (and the machinery and the papermaking clothing used to manufacture the capillary substrate) are selected based upon the needs of the consumer. The processes used to make the capillary substrate are often custom designed to meet the tradeoffs inherent in balancing the different properties (e.g., tensile strength, softness, absorbency) which affect the consumers' likes and dislikes, and ultimately the sales of the absorbent structure incorporating the capillary substrate. However, difficulties can arise in the prior art methods of applying the liquid precursor to the capillary substrate.

For example, it is difficult to spray the liquid precursor onto the substrate in a precise pattern. Printing the osmotic absorbent onto the substrate may result in a pattern having greater definition and precision than obtainable by spraying, but requires a printing roll having raised protuberances or gravure cells. Printing rolls having raised protuberances and gravure plates limit the pattern of the applied osmotic absorbent to that pattern corresponding to the protuberances of the printing roll or the gravure plates, regardless of which pattern may be desirable for a particular capillary substrate.

This problem may be overcome by providing a plethora of printing rolls and gravure plates, one for each desired pattern. However, such provision increases the expense of the apparatus to a point where it may not be economically feasible to provide a printing roll or a gravure plate for each desired pattern if only a short production run is desired.

Furthermore, the substrates disclosed in the prior art often exacerbate the gel blocking problem. The common uniform basis weight and uniform density capillary substrates provide equal capillary absorption in the X-Y plane. Insults of liquid deposited onto such a capillary substrate wick throughout all regions of the capillary substrate. Such wicking may transport the liquids into a region which is already gel blocked. Alternatively, the capillary absorbent may not compete sufficiently with the osmotic absorbent material to fully utilize the entire capacity of the absorbent structure.

Yet other problems encountered in the prior art include migration of the liquid precursor after it is applied to the capillary substrate. Such migration occurs in the X-Y plane. X-Y migration diminishes the differences in the pattern between the areas of the capillary substrate to which the liquid precursor was and was not applied.

Migration of the liquid precursor also occurs in the Z-direction, normal to the plane of the capillary substrate. Z-direction migration causes the liquid precursor to penetrate the thickness of the capillary substrate, to a uniform distribution between both faces of the capillary substrate. This uniform Z-direction distribution may limit the free swelling of the osmotic absorbent resulting from the liquid precursor, limiting its ability to absorb further liquid insults.

Unfortunately, physical constraints imposed by the capillary substrate itself which surrounds the osmotic absorbent distributed in the Z-direction, limit its ability to swell in the presence of liquid insults. Such limitations are directly proportional to the density of the capillary substrate into which the osmotic absorbent is disposed and are inversely proportional to the quantity and extent of the osmotic absorbent disposed out of the plane of the capillary substrate in the Z-direction.

Accordingly, it is an object of this invention to provide an absorbent structure which minimizes gel blocking by providing a pattern of an osmotic absorbent on a capillary substrate. Further, it is an object of this invention to provide an absorbent structure which allows swelling of the osmotic absorbent to occur without constraints being imposed by the capillary substrate. Finally, it is an object of this invention to provide an absorbent structure having a relatively high absorbency rate for a given gel strength by providing a favorable surface area to mass ratio.

SUMMARY OF THE INVENTION

The invention is an absorbent structure comprising a multi-topography substrate. The substrate may have two elevations, a first elevation defining a first pattern and a second elevation defining a second pattern. Each elevation comprises one or more regions. An immobilized osmotic absorbent is disposed on one or more of the regions corresponding to one of the elevations of the substrate. Preferably the substrate is a capillary substrate.

BRIEF DESCRIPTION OF THE DRAWINGS

While the Specification concludes with claims particularly pointing out and distinctly claiming the present invention, it is believed the present invention will be better understood from the following description taken in conjunction with the accompanying drawings in which:

DETAILED DESCRIPTION OF THE INVENTION

Figure 1:
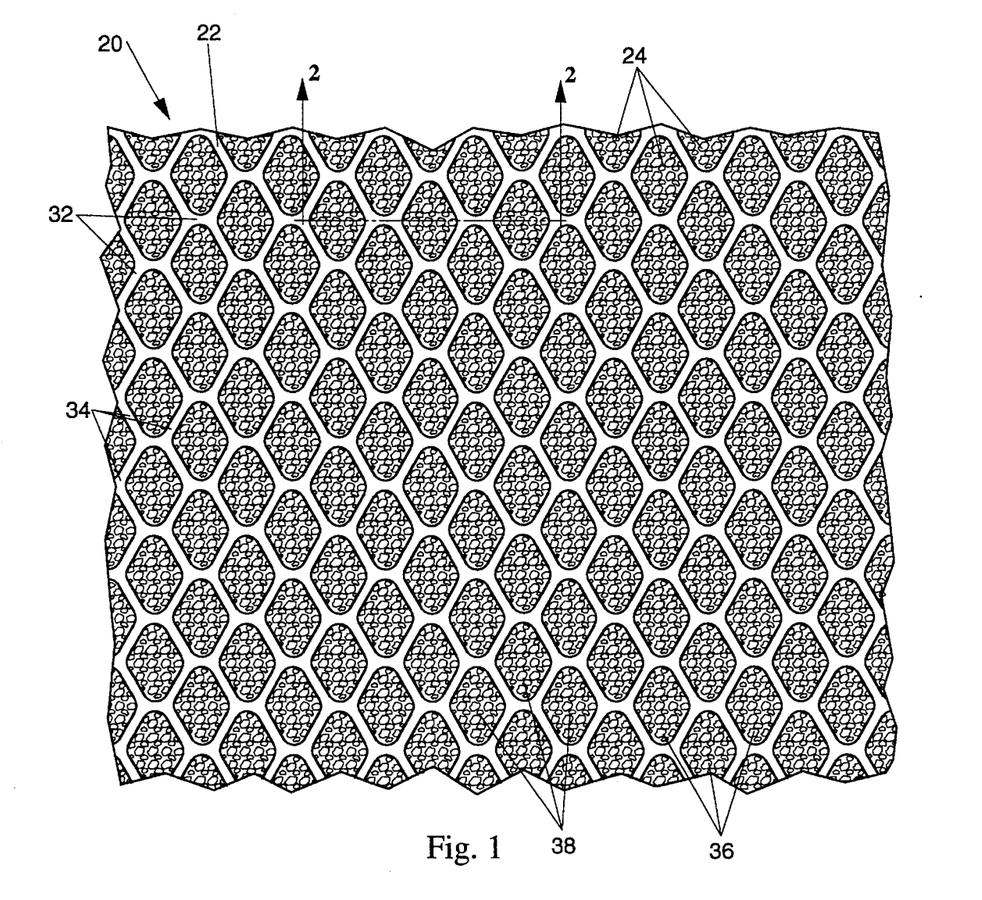
FIG. 1 is a fragmentary top plan view of an absorbent structure according to the present invention having a continuous capillary network and discrete sites of osmotic absorbent material therein.
Figure 3:
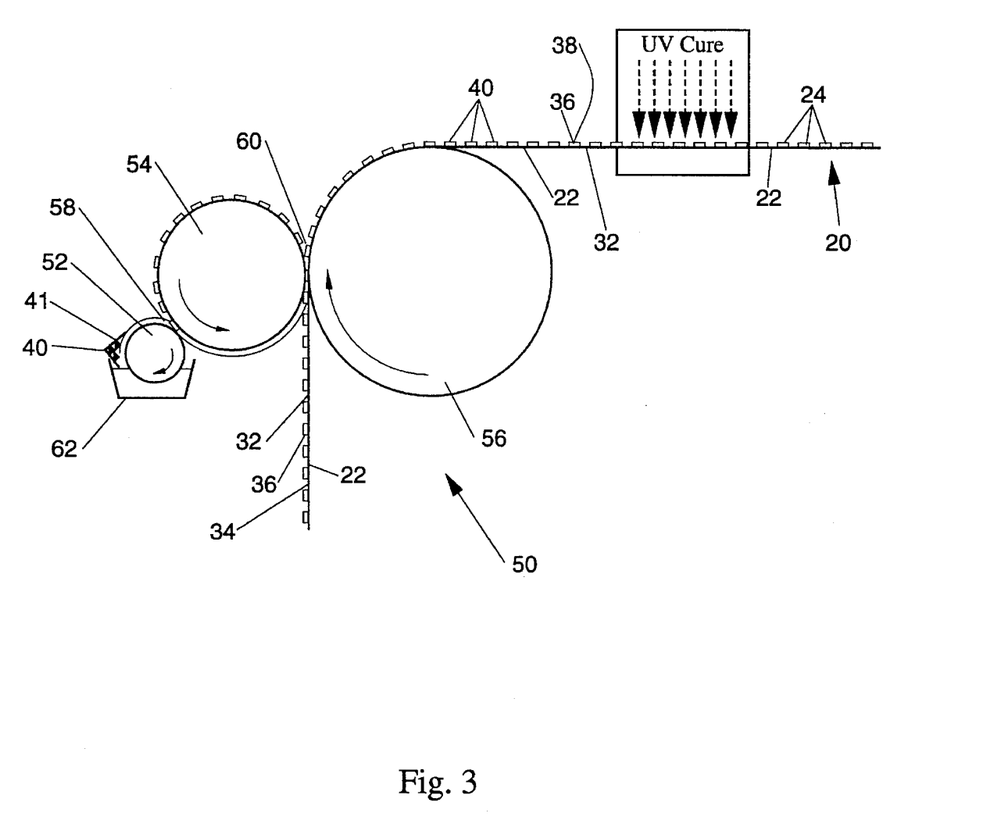
FIG. 3 is a schematic vertical elevational view of one apparatus which may be used to produce the structure of the present invention.

As illustrated in FIG. 1, an absorbent structure 20 according to the present invention comprises a generally planar substrate, preferably a capillary substrate 22, and an osmotic absorbent 24. The osmotic absorbent 24 is applied to the capillary substrate 22 as an osmotic absorbent precursor, typically in the form of a liquid precursor 40. Referring to FIG. 3, the liquid precursor 40 is applied to the capillary substrate 22 in a particular pattern. Once the liquid precursor 40 is disposed on the capillary substrate 22, the liquid precursor 40 is immobilized by in situ polymerization to form the osmotic absorbent 24.

Referring back to FIG. 1, the capillary substrate 22 is a capillary absorbent and preferably, though not necessarily, cellulosic. The capillary substrate 22 comprises multiple regions 34 and 38 having different basis weights and/or densities. Any arrangement of regions 34 and 38 in the capillary substrate 22 is acceptable, so long as the capillary substrate 22 is macroscopically planar, the osmotic absorbent 24 may be immobilized thereon, and the capillary substrate 22 absorbs and transports liquids deposited thereon by capillary (surface energy and wicking) mechanisms.

The capillary substrate 22 according to the present invention has distinguishable regions 34 and 38 defining two mutually different densities. Preferably, the regions 34 and 38 are disposed in an arrangement comprising an essentially continuous network region 32 and discrete regions 36 within the essentially continuous network. As used herein, a region 32 which extends substantially throughout the capillary substrate 22 in one or both of the principal dimensions is considered to be "an essentially continuous network." Conversely, regions 36 which are not contiguous, are considered to be "discrete." The discrete regions 36 project outwardly tom the region 32 defining the essentially continuous network to a distal end.

More preferably the regions 32 and 36 of the capillary substrate 22 are disposed in an arrangement having a high density essentially continuous network region 34 and discrete low density regions 38 within the essentially continuous network. This arrangement provides the advantage that the high density regions 34 forming the essentially continuous network 32 provides for efficacious transport of liquid insults to various discrete regions 36 having osmotic absorbent 24 thereon. Should one discrete region 36 of osmotic absorbent 24 absorb its full capacity of liquids, the excess liquids can be transported by capillary attraction through the high density regions 34 of the essentially continuous network 32 to other discrete regions 36 of osmotic absorbent 24.

For the embodiments described herein, a capillary substrate 22 having about 2 to about 155 low density discrete regions 36 (preferably with osmotic absorbent 24 thereon) per square centimeter (10 to 1000 discrete regions 36 per square inch) and more particularly, about 4 to about 39 low density discrete regions 36 per square centimeter (25 to 250 discrete regions 36 per square inch) has been found suitable.

The capillary substrate 22 according to the present invention has a topography which may comprise at least two different elevations 26. The "elevation" of a capillary substrate 22 is its local deviation from planarity. The elevation 26 of a substrate is determined by laying it on a flat, horizontal surface, which serves as a reference plane. Different elevations 26 of the capillary substrate 22, which may or may not be coincident with the regions 34 and 38 of differing density described above, are determined by the difference in height above the reference plane, taken orthogonal the reference plane and principal dimensions of the capillary substrate 22.

Preferably the regions 34 and 38 defined according to differing densities and differing elevations 26 are coincident. Thus the discrete low density regions 36 are also raised in elevation 26 (or lowered in elevation 26 if the capillary substrate 22 is inverted) from the high density regions 34 of the essentially continuous network region 32. However, it is to be recognized that suitable embodiments may exist wherein such discrete regions 36 of a particular density are not coincident with a particular elevation 26.

A particularly preferred capillary substrate 22 is through-air dried and produced in accordance with commonly assigned U.S. Pat. No. 4,529,480 issued Jul. 16, 1985 to Trokhan, which patent is incorporated herein by reference for the purpose of showing a through-air-dried capillary substrate 22 having discrete regions 36 and an essentially continuous pattern and for the purpose of showing how to make a particularly preferred capillary substrate 22 according to the present invention having different elevations. A capillary substrate 22 made according to U.S. Pat. No. 4,529,480 issued to Trokhan has mutually coincident discrete regions 36, which regions 36 are both relatively low in density and raised (or lowered) in elevation 26.

The capillary substrate 22 according to the present invention may be comprised of cellulosic fibers having one very large dimension (along the longitudinal axis of the fiber) compared to the other two relatively very small dimensions (mutually perpendicular, and being both radial and perpendicular to the longitudinal axis of the fiber), so that linearity is approximated. While microscopic examination of the fibers may reveal the other two dimensions are small compared to the principal dimension of the fibers, such other two small dimensions need not be substantially equivalent nor constant throughout the axial length of the fiber. It is only important that the fiber be able to bend about its axis, be able to bond to other fibers and be distributed onto a forming wire (or its equivalent) by a liquid carrier.

The capillary substrate 22 may be creped or be uncreped, as desired. Creping the capillary substrate 22 foreshortens it producing undulations in the Z-direction throughout the essentially continuous network region 32. Such undulations yield cross machine ripples which are considered too minor to be differences in elevation 26 as compared to the differences in elevation 26 obtainable by the methods described hereinbelow. However, it is to be recognized that a creped capillary substrate 22 may be embossed, through-air-dried, etc. to produce differences in elevation 26 which are large, relative to the creping undulations and ripples.

The fibers comprising the capillary substrate 22 may be synthetic, such as polyolefin or polyester; are preferably cellulosic, such as cotton linters, rayon or bagasse; and more preferably are wood pulp, such as soft woods (gymnosperms or coniferous) or hard woods (angiosperms or deciduous), may be cross-linked, and may comprise combinations of synthetic and cellulosic materials. As used herein, a capillary substrate 22 is considered "cellulosic" if the capillary substrate 22 comprises at least about 50 weight percent or at least about 50 volume percent cellulosic fibers, including but not limited to those fibers listed above. A cellulosic mixture of wood pulp fibers comprising softwood fibers having a length of about 2.0 to about 4.5 millimeters and a diameter of about 25 to about 50 micrometers, and hardwood fibers having a length of less than about 1 millimeter and a diameter of about 12 to about 25 micrometers has been found to work well for the capillary substrates 22 described herein.

If wood pulp fibers are selected for the capillary substrate 22, the fibers may be produced by any pulping process including chemical processes, such as sulfite, sulfate and soda processes; and mechanical processes such as stone groundwood. Alternatively, the fibers may be produced by combinations of chemical and mechanical processes or may be recycled. The type, combination, and processing of the fibers used are not critical to the present invention.

A capillary substrate 22 according to the present invention is macroscopically two-dimensional and planar, having some thickness in the third dimension. However, the thickness in the third dimension is relatively small compared to the first two dimensions or to the capability to manufacture a capillary substrate 22 having relatively large measurements in the first two dimensions.

The capillary substrate 22 according to the present invention comprises a single lamina and may be layered or stratified as to fiber type. However, it is to be recognized that two or more single laminae, any or all made according to the present invention, may be joined in face-to-face relation to form a unitary laminate.

Of course, it is to be recognized that a woven or nonwoven material may be adequately utilized as a capillary substrate 22, providing it meets the elevation requirements specified above.

The osmotic absorbent 24 may comprise any osmotic precursor, typically a liquid precursor 40, which can be applied to the capillary substrate 22 as illustrated in FIG. 3. As used herein a "precursor" refers to any material which transforms to an osmotic absorbent 24 upon curing or polymerizing. As used herein an "osmotic absorbent" refers to any material which has the capability to absorb at least 10 times its own weight of any aqueous solution, and preferably synthetic urine, on a grams per gram basis.

The synthetic urine comprises a salt solution in distilled water with a surface tension adjusted to 45 dynes per centimeter with about 0.0025% octylphenoxy polyethoxy ethanol surfactant (Triton X-100, from Rohm and Haas Company). The synthetic urine solution comprises 15 parts of 1% Triton X-100, 60 parts NaCl, 1.8 parts of $CaCl_2.2H_2O$, 3.6 parts of $MgCl_2.6H_2O$ and 6000 parts of distilled water.

Preferred osmotic absorbents 24 include copolymers of sodium acrylate and acrylic acid, starch grafted acrylate copolymers, cross-linked carboxymethyl cellulose, etc. Any liquid precursor 40 which can be cured into a solid osmotic absorbent 24 is suitable. A particularly preferred liquid precursor 40, and ultimately osmotic absorbent 24 for use in the present invention, comprises polymers of sodium acrylate, and acrylic acid, carboxymethyl cellulose, a photo-initiator and a cross-linker.

A preferred liquid precursor 40 is a substantially water-soluble monomer comprising neutralized or neutralizable carboxyl groups. The monomer preferably contains sufficient carboxyl groups such that a linear polymer thereof is substantially water-soluble (i.e., the carboxyl groups are hydrophilic). Mixtures of such monomers may also be used.

The monomers comprising carboxyl groups include acid, acid anhydride, and ester group containing monomers. These monomers may also contain other hydrophilic groups, such as hydroxyl groups, amide-groups, amino groups, nitrile groups, and quaternary ammonium salt groups. Preferably, the monomer contains acid type hydrophilic groups. More preferably, the monomer contains at least about 5 mole percent, most preferably at least about 10 mole percent, of acid groups.

Monomers containing carboxyl groups include the olefinically unsaturated acids, esters thereof, and anhydrides which contain at least one carbon to carbon olefinic double bond. More specifically, these monomers can be selected from olefinically unsaturated carboxylic acids, esters of such carboxylic acids, acid anhydrides, sulfonic acids, esters of such sulfonic acids, and mixtures of any two or more of the foregoing monomers.

Olefinically unsaturated carboxylic acid and carboxylic acid anhydride monomers include the acrylic acids and derivatives thereof, typified by acrylic acid itself, methacrylic acid, ethacrylic acid, alpha-chloroacrylic acid, alpha-cyano acrylic acid, beta-methyl acrylic acid (i.e., crotonic acid), alpha-phenyl acrylic acid, beta-acryloxy propionic acid, and beta-steryl acrylic acid; maleic acid; and maleic anhydride. Other monomers of this type are sorbic acid, alpha-chloro sorbic acid, angelic acid, cinnamic acid, p-chloro cinnamic acid, itaconic acid, citraconic acid, mesaconic acid, glutaconic acid, aconitic acid, fumaric acid, and tricarboxyethylene.

Olefinically unsaturated sulfonic acid monomers and derivatives thereof include aliphatic or aromatic vinyl sulfonic acids such as vinylsulfonic acid, allyl sulfonic acid, vinyltoluene sulfonic acid and styrene sulfonic acid; and acrylic and methacrylic sulfonic acid derivatives such as sulfoethyl acrylate, sulfoethyl methacrylate, sulfopropyl acrylate, sulfopropyl methacrylate, 2-hydroxy-3-acryloxy propyl sulfonic acid, 2-hydroxy-3-methacryloxy propyl sulfonic acid and 2-acrylamido-2-methyl propane sulfonic acid.

The carboxyl groups (e.g., acid groups) are at least partially neutralized with cations capable of forming a salt with the monomer to form a monomer having neutralized carboxyl groups. Such salt-forming cations include, for example, alkali or alkaline metals, ammonium, substituted ammonium and amines as discussed in further detail in U.S. Pat. No. Re. 32,649, Brandt et al., Apr. 19, 1988, incorporated herein by reference for the purpose of showing suitable osmotic absorbents 24. Neutralization is preferably carried out in any conventional manner which results in at least about 25 mole percent, more preferably at least about 50 mole percent, most preferably at least about 75 mole percent, of the total carboxyl groups being neutralized. The carboxyl groups are preferably neutralized prior to formation of the substantially water-insoluble polymer foam, e.g., neutralization is preferably carried out on the monomer or of a water-soluble polymer thereof.

Monomers possessing hydrophilic groups other than carboxyl groups may be used with the carboxyl group containing monomer. Other hydrophilic groups include hydroxyl groups, amide-groups, amino groups, nitrile groups, and quaternary ammonium salt groups. Monomers containing such groups are well known materials and are described in greater detail, for example, in U.S. Pat. No. 4,076,663 issued to Masuda et al. on Feb. 28, 1978; and U.S. Pat. No. 4,062,817 issued to Westerman on Dec. 13, 1977; which patents are incorporated herein by reference. One or more types of such hydrophilic groups may be present in the monomer.

Although this disclosure is generally in terms of the liquid precursor 40, it is to be understood that substantially water-soluble homopolymers, copolymers, or reaction products of the monomer may also be used in place of or in addition to the monomer form. Such alternative starting materials include substantially water-soluble homopolymers of the monomer and substantially water-soluble reaction products of the monomer or its homopolymer and the internal crosslinking agent. For example, a substantially linear, substantially water-soluble osmotic absorbent 24 can be formed by subjecting the liquid precursor 40 to known polymerization conditions. A substantially water-soluble, partially crosslinked osmotic absorbent 24 may also be formed by reacting (e.g., by heating) the liquid precursor 40 or linear polymer thereof with a crosslinking agent such as the crosslinking agents herein. Such a osmotic absorbent 24 would typically have a low level of crosslinking, e.g., less than about 5%.

The specific type of liquid precursor 40 selected is not critical to the invention, so long as the liquid precursor 40 may be applied in the desired pattern, and immobilized, so that the liquid precursor 40 does not flow, migrate, or otherwise transport to different parts of the capillary substrate 22 and transmogrify the desired pattern into a less useful disposition of the liquid precursor 40 (such as a uniform coating or a coating disposed on regions 32 of an elevation 26, which are desired to be free of the liquid precursor 40). The osmotic absorbent 24 is preferably immobilized in both the dry condition and while wetted in use. Such transmogrification may result in an absorbent structure 20 which encounters gel blocking due to the swelling of the osmotic absorbent 24 which occurs upon imbibing liquids and may further result in gel contacting the skin of the user or wearer.

The osmotic absorbent 24 may be applied to the capillary substrate 22 in liquid form, such as the liquid precursor 40 discussed above. Preferably when applied to the capillary substrate 22 the liquid precursor 40 has a kinematic viscosity of at least about 2,000 centipoises, as measured by a Brookfield viscometer using a number 2 Shell cup at 20 degrees C. and preferably a kinematic; viscosity of at least about 4,000 centipoises. Such a viscosity is necessary to hold the liquid precursor 40 in place until it is cured into a solid osmotic absorbent 24 polymer by crosslinking.

A kinematic viscosity of at least about 2,000 centipoises may be achieved by adding a thickening agent to the liquid precursor 40 prior to its application to the capillary substrate 22. Suitable thickening agents include polyvinyl pyrolodine, hydroxyethyl cellulose, preferably carboxymethyl cellulose and polyacrylic acid. The thickening agent may be added in a concentration of 2 percent by weight of thickening agent to the liquid precursor 40.

If one does not wish to add a thickening agent to the liquid precursor 40, an acrylic acid type liquid precursor 40 can be utilized and partially prepolymerized. Prepolymerization not only increases the viscosity but also allows for removal of residual monomers before the liquid precursor 40 is applied to the capillary substrate 22. Minimizing residual monomers in the resulting osmotic absorbent 24 is highly desirable if the absorbent structure 20 is to be utilized in a disposable absorbent article, such as a diaper or sanitary napkin, or is to be utilized in other applications where epidermal contact may occur.

Figure 2:
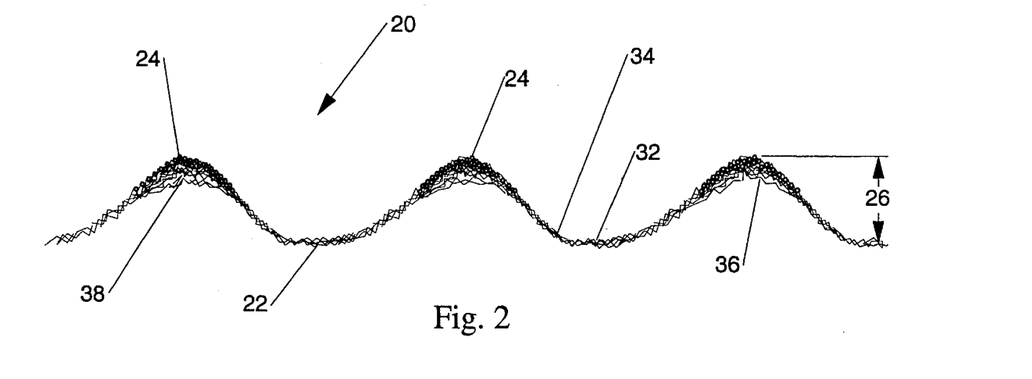
FIG. 2 is a fragmentary side elevational view taken along line 2—2 of FIG. 1.

Referring to FIG. 2, the liquid precursor 40, and hence the resulting polymerized osmotic absorbent 24, is preferably disposed upon, registered with, and immobilized at the discrete low density regions 38 of the capillary substrate 22 in a particular predetermined pattern. Although other patterns, such as semicontinuous patterns which form lines extending throughout substantially only one principal dimension of the capillary substrate 22 (i.e., the machine direction, the cross machine direction, or diagonals thereof) are possible, a pattern having the osmotic absorbent 24 disposed on only the discrete low density regions 38 is preferred.

This pattern allows for absorption of liquids deposited thereon and swelling of the osmotic absorbent 24 in the three principal dimensions corresponding to the plane and elevation 26 of the capillary substrate 22, yet accommodates capillary transport of liquids to other discrete low density regions 38 having the osmotic absorbents 24. Such accommodation occurs because the spacing between the discrete regions 36 allows swelling of the osmotic absorbent 24, without obstructing capillary transport of the liquids and because the swollen osmotic absorbent 24 remains immobilized on the capillary substrate 22 after absorbing the liquid deposited thereon.

The liquid precursor 40 (which is cured to become an osmotic absorbent 24) may preferably be applied to the topographically elevated portions of the capillary substrate 22. This arrangement provides the advantage of a somewhat three-dimensional absorbent structure 20, so that liquid insults normal to the plane of the capillary substrate 22 first strike the osmotic absorbent 24, begin the swelling process, then run off the osmotic absorbent 24 and into the capillary channels of the essentially continuous network of the capillary substrate 22. This arrangement is even more efficacious if the capillary substrate 22 has the high density essentially continuous network region 32 described above.

Preferably, the liquid precursor 40 cures to a generally flat-shaped discrete region 36 of osmotic absorbent 24. A flat-shaped osmotic absorbent 24 has a more favorable surface area to mass ratio, thereby increasing the rate of fluid absorption and allowing greater unconstrained expansion, and thus :reducing the tendency for gel blocking to occur than does other shapes of a cured osmotic absorbent 24. Interfiber penetration of the capillary substrate 22 into the osmotic absorbent 24 increases the acquisition rate of absorption, aids in obtaining more complete utilization of the osmotic absorbent 24, and immobilizes the osmotic absorbent 24 with respect to the substrate 22.

The freestanding osmotic absorbent 24 is in situ polymerized, to prevent it from wicking throughout the capillary substrate 22. In situ polymerization may be accomplished by irradiating the osmotic absorbent 24 under radiation having a wave length sufficient to crosslink and cure the osmotic absorbent 24. Typically, ultraviolet light has been found to work well.

Increasing the viscosity of the liquid precursor 40 to at least 2,000 centipoises prior to deposition on the capillary substrate 22 also retards separation of the various components of the liquid precursor 40. By retarding such separation, or chromatographing of the components of the liquid precursor 40, the desired reaction mixture is maintained during polymerization. For example, in aqueous liquid precursors 40 the proper amount of water is maintained to prevent component polymerizable material from becoming insolubilized. Insolubilized polymerizable material negatively affects the polymerization reaction, and hence the ultimate performance of the osmotic absorbent 24.

Prepolymerization or use of a thickening agent retards the movement of the liquid precursor 40 prior to polymerization. Such retarding is highly desirable in production of the absorbent structure 20 according to the present invention. This desirability is due to the thermodynamically unfavored application of the liquid precursor 40 to the low density regions 38. In the absence of restraining forces, the liquid precursor 40 will, through capillary attraction, wick into the high density regions 34, and the balance of the capillary substrate 22 until equilibrium occurs.

Increasing the viscosity of the liquid precursor 40 to at least 2,000 centipoises and preferably to at least 4,000 centipoises (or prepolymerizing the liquid precursor 40) prior to its deposition on the capillary substrate 22 retards and hence minimizes the resulting wicking of the liquid precursor 40, as described above. By retarding such wicking, the desired patterned application of the liquid precursor 40 is maintained after the liquid precursor 40 cures to an osmotic absorbent 24. Thus, the desired permanent registration of the osmotic absorbent 24 with particular regions of the capillary substrate 22, particularly the low density regions 38, can be more accurately and repeatably achieved.

Increasing the viscosity of the liquid precursor 40 to at least 2,000 centipoises prior to deposition on the capillary substrate 22 also retards separation of the various components of the liquid precursor 40. By retarding such separation, or chromatographing of the components of the liquid precursor 40, the desired reaction mixture is maintained during polymerization. For example, in aqueous precursors the proper amount of water is maintained to prevent component polymerizable material from becoming insolubilized. Insolubilized polymerizable material negatively affects the polymerization reaction, and hence the ultimate performance of the osmotic absorbent 24.

After the liquid precursor 40 is applied to the capillary substrate 22, the liquid precursor 40 is immobilized by curing. Curing and immobilization may be accomplished using any suitable technique as is well known in the art, such as heat, electron beam irradiation or ultraviolet radiation. It is desirable that the liquid precursor 40 be cured to an osmotic absorbent 24 as soon as possible after its application to the capillary substrate 22, minimizing the opportunity for the liquid precursor 40 to flow into the thermodynamically favored high density essentially continuous network of the capillary substrate 22 (or into any other regions of the capillary substrate 22).

Curing of the liquid precursor 40 can be accomplished by any means that initiates and causes polymerization. If a free radical initiator such as 2-hydroxy-iso-butyrophenone or 2,2-azobis(2-amidino propane)dihydrochloride is included in a monomer forming the liquid precursor 40, heat, light (either visible or ultraviolet radiation), or ionizing radiation can initiate and cause the polymerization reaction. If one does not wish to include a free radical initiator, electron beam irradiation may be used to otherwise create free radicals which start the curing reaction. If one desires, an osmotic chemistry which does not utilize a free radical initiator may be incorporated, thereby allowing any other appropriate initiator to be used.

This curing process polymerizes and transforms the liquid precursor 40 into a solid osmotic absorbent 24 polymer. Thus according to the present invention, the liquid precursor 40 is polymerized in situ, without requiring an additional step between the application of the liquid precursor 40 and its polymerization to dispose and immobilize the osmotic absorbent 24 on the capillary substrate 22 in the desired location and pattern.

Referring again to FIG. 3, the absorbent structure 20 according to the present invention may be made according to the illustrated apparatus 50. The illustrated apparatus 50 comprises three axially rotatable rolls 52, 54 and 56, preferably having mutually parallel longitudinal axes, a metering roll 52, a transfer roll 54, and an anvil roll 56. The three rolls 52, 54 and 56 form a nip 58 and a gap 60. The nip 58 is between the metering roll 52 and the transfer roll 54. The gap 60 is between the transfer roll 54 and the anvil roll 56.

The metering roll 52 is a gravure roll disposed in a reservoir 62 of the liquid precursor 40. Upon axial rotation, the metering roll 52 transfers a particular quantity of the liquid precursor 40 to the transfer roll 54. The capillary substrate 22 passes through the gap 60 between the transfer roll 54 having liquid precursor 40 disposed thereon and the anvil roll 56. Importantly the topographically elevated regions 36 and 38 of the capillary substrate 22, to which it is desired to apply the liquid precursor 40, project towards and contact the transfer roll 54, with the balance of the capillary substrate 22 resting against the anvil roll 56. It will be apparent to one skilled in the art that by increasing or decreasing the clearance in the gap 60 between the transfer roll 54 and the anvil roll 56, smaller and larger amounts of the liquid precursor 40 may be printed upon and applied to the topographically elevated regions of the capillary substrate 22, respectively, upon contact therewith. Likewise, changing the design of the metering roll 52 can alter the amount of liquid precursor 40 applied to the capillary substrate 22 at a constant gap 60. Alternatively, it will be apparent the liquid precursor 40 may be applied to the transfer roll 54 by spraying, submerging the transfer roll 54 in the liquid precursor 40, etc., and thereby eliminating the necessity for a metering roll 52, or by printing directly from the metering roll 52 to the substrate 22 in the gap 60 formed between the metering roll 52 and the anvil roll 56.

As the capillary substrate 22 passes through the gap 60 between the transfer roll 54 and the anvil roll 56, liquid precursor 40 is applied to only the regions of the capillary substrate 22 which have an elevation 26 sufficient to contact the periphery of the transfer roll 54. The transfer roll 54, does not contact the portions of the capillary substrate 22 which rest against the anvil roll 56. Accordingly, no liquid precursor 40 is applied to these portions of the capillary substrate 22.

By adjusting the clearance in the gap 60, different quantities of the liquid precursor 40, and ultimately cured osmotic absorbent 24, may be applied to the elevated regions of the capillary substrate 22. Generally, for the embodiments described herein, liquid precursor 40 applied in the range of about 0.1 to about 5 grams per square meter of discrete region 36 has been found suitable.

Generally, a greater quantity of osmotic absorbent 24 should be present on the capillary substrate 22 if the end use of the absorbent structure 20 dictates it will handle larger volumes of fluid. Generally a lesser quantity of the osmotic absorbent 24 should be present on the capillary substrate 22 if the end use of the absorbent structure 20 dictates concerns with gel blocking or the ability to rapidly transport liquid insults to other areas of the absorbent structure 20.

Once the capillary substrate 22 to be utilized in the absorbent structure 20 is selected based upon consumer preferences, certain benefits become apparent. Particularly, the capillary substrate 22 according to the present invention, having regions 32 and 36 of different elevations 26 (one region 32 in contact with the anvil roll 56, the other region 36 in contact with the transfer roll 54) provides several advantages not found in the prior art. First, a particular pattern of the liquid precursor 40 may be deposited onto the capillary substrate 22, without requiring the transfer roll 54 to have a gravure plate or have radially extending protuberances. Typically, metering rolls 54 having patterns are more difficult and expensive to manufacture, than smooth surface metering rolls 54.

A second benefit of the claimed invention is the flexibility which allows one who may not wish to use an transfer roll 54 having a pattern, to achieve registration of the pattern with the regions of the capillary substrate 22 to which it is desired to apply the liquid precursor 40. Such registration can be extremely difficult to achieve under even ideal manufacturing conditions, as the different regions of the capillary substrate 22 may occur on near microscopic scale. Actual manufacturing is even more complex, because the pitch of the different regions 32 and 36, and hence the opportunity of misregistration may change with ordinary variations in tension as the capillary substrate 22 is drawn through the apparatus 50, the basis weight of the capillary substrate 22, and other manufacturing parameters. Production of the invention by the process described in FIG. 3 ensures exact registration of the liquid precursor 40 with the desired regions of the capillary substrate 22.

Third, if it is desired to change the pattern of liquid precursor 40 applied to the capillary substrate 22, a single apparatus 50 having a transfer roll 54 with a smooth periphery may be utilized for multiple patterns. A capillary substrate 22 having a different topography is inserted in the gap 60 between the transfer roll 54 and anvil roll 56, and the clearance of the gap 60 adjusted as appropriate. The transfer roll 54 may continue to be provided with a smooth surface and any desired pattern achieved by simply changing the capillary substrate 22. Once a particular capillary substrate 22 is selected, such flexibility in manufacturing was unattainable in the prior art.

Several variations according to the present invention are feasible. For example, if desired, one may construct a capillary substrate 22 having an essentially continuous network region 32 and discrete regions 36 which differ according to basis weight rather than density. If such a capillary substrate 22 is selected, it may be advantageously made using a forming wire according to FIG. 4 of commonly assigned U.S. Pat. No. 4,514,345 issued Apr. 30, 1985 to Johnson et al., or the forming wires disclosed in U.S. Pat. No. 5,245,025 issued Sep. 14, 1993 to Trokhan et al., which patents are incorporated herein by reference for the purpose of showing how to make a capillary substrate 22 having regions which differ according to basis weight. Alternatively, discrete regions 36 having plural different elevations 26 above (or below) the essentially continuous network region 32 are feasible. The osmotic absorbent 24 may be applied to only the discrete regions 36 having a particular minimum elevation 26, or to each of the discrete regions 36 in elevation 26 dependent quantities.

Another variation involves the liquid precursor 40 which ultimately forms the osmotic absorbent 24. In this variation, it is recognized that osmotic absorbents 24 vary according to their gel strength—the ability to retain absorbed fluids in the presence of compressive forces. Osmotic absorbents 24 also vary according to acquisition rate—the speed at which fluids deposited onto the osmotic absorbent 24 can be acquired and held thereby, and gel volume—the amount of fluid absorbed on a grams per gram basis. Generally, the gel strength of an osmotic absorbent 24 is inversely proportional to its absorption rate and gel volume.

If desired, an osmotic absorbent 24 having a more rapid absorption rate may be utilized at or near the center of the absorbent structure 20. Prophetically, in such an embodiment liquid insults would be rapidly absorbed and not readily flow to the perimeter of the absorbent structure 20 where leakage may occur if the liquids breach the perimeter.

Alternatively, the absorbent structure 20 may have an osmotic absorbent 24 with a faster absorption rate near the perimeter. This arrangement prophetically provides the advantage that liquids near the perimeter of the absorbent structure 20 are rapidly absorbed before a breach of the perimeter can occur. Similarly, the osmotic absorbent 24 near the center of the absorbent structure 20 may have a relatively greater gel strength. The relatively greater gel strength provides for relatively greater retention of liquid insults which are deposited near the center of the absorbent structure 20, so that such absorbed insults are less likely to approach the perimeter of the absorbent structure 20.

At or near the perimeter, an osmotic absorbent 24 having a higher gel strength but slower acquisition rate may be utilized. This osmotic absorbent 24 provides for greater retention of absorbed liquids, but can accommodate the slower acquisition due to the insult only being received indirectly by the perimeter since the liquid insult first occurs at the higher absorption rate osmotic absorbent 24 disposed at or near the center of the absorbent structure 20.

An absorbent structure 20 having osmotic absorbents 24 of differing gel strengths and/or absorption rates may be made by utilizing plural reservoirs containing different liquid precursors. A particularly preferred arrangement has three reservoirs 62, spaced apart in the machine direction. The two outboard reservoirs 62 each contain identical liquid precursor 40 having a relatively higher gel strength but relatively slower absorption rate upon polymerization. The central reservoir 62 contains a liquid precursor 40 having a relatively faster absorption rate but relatively low gel strength upon polymerization.

Of course, it will be apparent to one skilled in the art that the three (or any other number as desired) independent reservoirs 62 need not be of equal width in the cross machine direction. The width of the reservoirs 62 may be adjusted, as desired, to tailor the absorbent characteristics of the capillary substrate 22 of the resulting absorbent structure 20 to the needs dictated by the end use of the absorbent structure 20. This arrangement provides a transverse gradient with respect to the absorption rate and gel strength properties of the osmotic absorbent 24 of the absorbent structure 20.

Such an arrangement of different osmotic absorbents 24 may be particularly useful if the absorbent structure 20 is incorporated into the core of a disposable absorbent article, such as a diaper, or a sanitary napkin. A disposable diaper utilizing the absorbent structure 20 of the present invention in the core may be made in accordance with commonly assigned U.S. Pat. No. 3,860,003 issued Jan. 14, 1975 to Buell. Of course, the disposable diaper can be sized and configured to fit either children or incontinent adults, as desired, and as used herein is inclusive of disposable absorbent articles worn by either children or adults. A sanitary napkin utilizing the absorbent structure 20 of the present invention in the core may be made in accordance with commonly assigned U.S. Pat. No. 4,950,264 issued Aug. 21, 1990 to Osborn, III, which two patents are incorporated herein by reference for the purpose of showing how to incorporate the absorbent structure 20 of the present invention into disposable absorbent articles, such as diapers and sanitary napkins. It will be apparent to one skilled in the art that several other variations are feasible, all of which are included within the scope of the appended claims.

What is claimed is:

1. An absorbent structure comprising:
   a fibrous capillary substrate having two elevations, a first elevation defining a first pattern and a second elevation defining a second pattern, each said elevation comprising one or more regions, said regions having two different densities, a relatively high density and a relatively low density, whereby said fibers of said substrate are deflected in said regions having said low density; and
   an immobilized osmotic absorbent cured in situ from a liquid precursor and disposed on one or more of said regions corresponding to one of said elevations of said capillary substrate.

2. The absorbent structure according to claim 1 wherein one of said elevations corresponds to discrete regions and the other of said elevations corresponds to an essentially continuous network.

3. The absorbent structure according to claim 2 wherein said immobilized osmotic absorbent is disposed on said discrete regions.

4. The absorbent structure according to claim 2 wherein said discrete regions have a lesser density than that of said essentially continuous network.

5. The absorbent structure according to claim 3 wherein said discrete regions have a lesser density than that of said essentially continuous network.

6. An absorbent structure according to claim 1 wherein at least one of said elevations defines a semicontinuous pattern.

7. An absorbent structure according to claim 4 wherein said osmotic absorbent is applied to one of said elevations of said semicontinuous patterns.

8. A disposable diaper having a core, wherein said core comprises an absorbent structure according to claim 1.

9. A disposable diaper having a core, wherein said core comprises an absorbent structure according to claim 2.

10. A disposable diaper having a core, wherein said core comprises an absorbent structure according to claim 3.

11. A sanitary napkin having a core, wherein said core comprises an absorbent structure according to claim 1.

12. A sanitary napkin having a core, wherein said core comprises an absorbent structure according to claim 2.

13. A sanitary napkin having a core, wherein said core comprises an absorbent structure according to claim 3.

14. A through-air-dried absorbent structure comprising:
    a fibrous capillary substrate having an essentially continuous network and discrete regions distributed therein, said essentially continuous network defining a first elevation and a plurality of said discrete regions defining a second elevation, said regions having two different densities, a relatively high density and a relatively low density, whereby said fibers of said substrate are deflected in said regions having said low density; and
    an immobilized osmotic absorbent cured in situ from a liquid precursor and disposed on one or more of said discrete regions.

15. An absorbent structure according to claim 14 wherein said discrete regions project outwardly from said essentially continuous network to a distal end, and said osmotic absorbent is disposed on said distal end.

16. An absorbent structure according to claim 1 made according to the method comprising the step of printing said osmotic absorbent onto said regions corresponding to one of said elevations of said capillary substrate by contact with a roll.

17. An absorbent structure according to claim 2 made according to the method comprising the step of printing said osmotic absorbent onto said regions corresponding to one of said elevations of said capillary substrate by contact with a roll.

18. An absorbent structure according to claim 14 made according to the method comprising the step of printing said osmotic absorbent onto said regions corresponding to one of said elevations of said capillary substrate by contact with a roll.

19. An absorbent structure according to claim 15 made according to the method comprising the step of printing said osmotic absorbent onto said regions corresponding to one of said elevations of said capillary substrate by contact with a roll.

* * * * *

UNITED STATES PATENT AND TRADEMARK OFFICE
CERTIFICATE OF CORRECTION

PATENT NO. : 5,487,736
DATED : May 5, 1996
INVENTOR(S) : Dean Van Phan

It is certified that error appears in the above-indentified patent and that said Letters Patent is hereby corrected as shown below:

Column 4, line 29, delete "tom" and insert --from--.

Signed and Sealed this

Twenty-ninth Day of April, 1997

Attest:

BRUCE LEHMAN

Attesting Officer      Commissioner of Patents and Trademarks